United States Patent [19]
Qian et al.

[11] Patent Number: 5,220,502
[45] Date of Patent: Jun. 15, 1993

[54] AUTOMATIC BLOOD PRESSURE MEASUREMENT IN HYPERBARIC CHAMBER

[75] Inventors: Zhenhai Qian, Branford; Robert Cousineau, Hamden, both of Conn.

[73] Assignee: CAS Medical Systems, Inc., Branford, Conn.

[21] Appl. No.: 597,492

[22] Filed: Oct. 10, 1990

[51] Int. Cl.⁵ .................. G06F 15/00; A61B 5/02; G01L 7/00
[52] U.S. Cl. .................. 364/413.03; 128/677; 128/205.26; 128/204.29; 73/706
[58] Field of Search .................. 364/413.13, 413.03; 128/205.26, 674, 677, 680, 681, 679, 204.29, ; 73/706

[56] References Cited
U.S. PATENT DOCUMENTS 4,625,277  11/1986  Pearce et al. .................. 364/413.03
4,633,859   1/1987  Reneau .................. 128/205.26
4,735,213   4/1988  Shirasaki .................. 364/413.03
4,754,406   6/1988  Miyawaki et al. .................. 364/413.13
4,796,184   1/1989  Bahr et al. .................. 364/413.13

Primary Examiner—Roy N. Envall, Jr.
Assistant Examiner—Frantzy Poinvil
Attorney, Agent, or Firm—William W. Jones

[57] ABSTRACT

Blood pressure measurements are performed on subjects disposed in hyperbaric chambers. The measurements are made by an automatic blood pressure monitoring instrument having a differential pressure transducer component. The pressure on the reference side of the pressure transducer is equal to the pressure in the hyperbaric chamber. The reference pressure is derived from a pressure source which equals the pressure in the hyperbaric chamber, but which pressure source does not contain the high purity oxygen gas in the hyperbaric chamber.

4 Claims, 1 Drawing Sheet

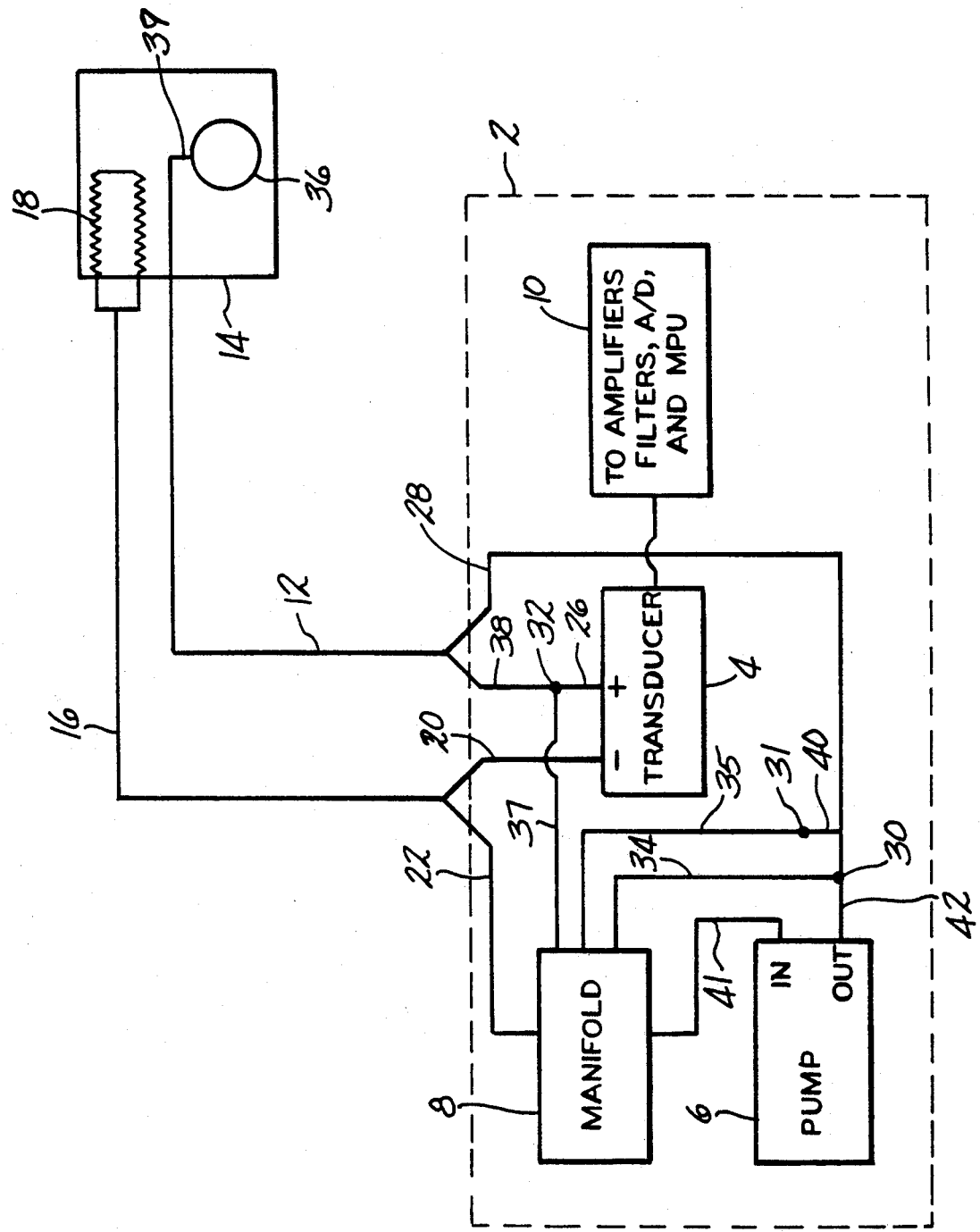

5,220,502

AUTOMATIC BLOOD PRESSURE MEASUREMENT IN HYPERBARIC CHAMBER

FIELD OF THE INVENTION

This invention relates to the automatic measurement of the blood pressure of a subject who is confined to a hyperbaric chamber.

DESCRIPTION OF RELATED ART

Hyperbaric chambers have been used for treating Caisson disease, or "bends" in deep sea divers, tunnel crew personnel, and the like persons exposed to high pressure environments. These chambers contain high purity oxygen at super atmospheric pressure, typically 3 ATM or greater.

Recently, it has been discovered that subjects who have undergone skin grafts will be benefitted by being placed in a hyperbaric chamber because the grafts heal faster in this high pressure pure oxygen environment. This latter use of the hyperbaric chamber requires that the subject remain in the chamber for longer periods of time than the Caisson disease treatment, and also involves subjects whose vital signs must be closely monitored.

Investigations are also ongoing relative to the use of hyperbaric chambers in the treatment of post heart attack victims. The latter treatment also requires extended periods of confinement in the hyperbaric chamber, and close monitoring of patient vital signs.

One of the vital signs which must be closely monitored is the subject's blood pressure. Most, if not all modern hospitals use automated blood pressure monitors on patients, which inflate the pressure cuff automatically periodically and measure and record the systolic, mean and diastolic blood pressure values of the patient. These devices typically include onboard microprocessors, pumps and electrically operated valves for controlling gas flow, and for taking and storing pressure values. A differential pressure transducer is included to measure cuff pressures and cuff pressure oscillations caused by arterial pulses. Up to the present time these automatic blood pressure monitors have not been suitable for use in hyperbaric chambers because of inflation problems which can only be overcome by using inordinately large pumps when the monitor is outside of the chamber because of the need to overcome chamber pressure with ambient air pumped into the cuff; and because the pure oxygen atmosphere precludes placing the monitor inside of the chamber.

U.S. patent application Ser. No. 410,130, filed Sep. 20, 1989 discloses a blood pressure monitor suitable for use in a hyperbaric chamber.

SUMMARY OF THE INVENTION

This invention relates to an improvement to the aforesaid automatic blood pressure monitoring instrument that can be used to monitor the blood pressure of a subject who is confined to a hyperbaric chamber. The instrument includes an onboard microprocessor; an inflation pump; inflation gas flow control valves; and a differential pressure transducer, all contained in a portable housing which is positioned outside of the hyperbaric chamber. The pressure cuff is, of course, inside of the chamber. The inflation pump and deflation valves are connected by inflate hoses to the cuff, and the sensor side of the pressure transducer is also connected to the inflate hoses. The exhaust valves are connected to a gas pressure source which is equal to the pressure inside the hyperbaric chamber through an exhaust hose. The instrument does not use the pure oxygen from the chamber, and thus does not expose any of the electrical or other components of the device to pure oxygen. Thus the cuff is inflated with gas from the reference gas pressure source, and is deflated back into the reference gas pressure source. The exhaust hose is also connected to the reference side of the differential pressure transducer whereby the transducer can accurately measure cuff pressures with reference to the chamber pressure which acts on the exterior of the cuff, since the pressure in the reference gas pressure source equals the pressure in the hyperbaric chamber. The differential between the chamber pressure and cuff pressure is thus registered as "Cuff pressure". Inflating the cuff with gas having a pressure equal to that inside of the chamber overcomes the problem of the high pressure acting on the outside of the cuff.

DESCRIPTION OF SPECIFIC EMBODIMENTS

It is therefore an object of this invention to provide an automatic blood pressure monitor which can be used to monitor the blood pressure of a subject who is confined to a hyperbaric chamber.

It is a further object of this invention to provide a blood pressure monitor of the character described which inflates the pressure cuff with gas having a pressure equal to that in the hyperbaric chamber, but which is not high purity oxygen.

It is an additional object of this invention to provide a blood pressure monitor of the character described which uses a differential pressure transducer referenced to the hyperbaric chamber pressure to sense cuff pressure and arterial cuff pressure oscillations.

These and other objects and advantages of the invention will become more readily apparent from the following detailed description thereof when taken in conjunction with the accompanying drawing which is a schematic representation of a preferred embodiment of the invention.

BRIEF DESCRIPTION OF THE DRAWING

The mechanical and electrical components of the device are contained in a casing 2 and are similiar to those shown in U.S. Pat. No. 4,796,184, granted Jan. 3, 1989 which is incorporated hereinto in its entirety. Inside of the casing 2 is a differential pressure transducer 4, a pump 6, and gas flow manifold 8. The pressure transducer 4 is connected to the electronic components 10 of the instrument for data acquisition and display. An inflating/sensing line or hose 12 extends from the casing 2 to the hyperbaric chamber 14, and an exhaust/reference line or hose 16 extends between the hyperbaric chamber 14 and the casing 2. The exhaust hose 16 opens into the interior of a flexible reference gas chamber 18 disposed in the hyperbaric chamber 14, and opens into the negative or reference side of the pressure transducer 4 via hose 20. An exhaust hose 22 connects the manifold 8 with the exhaust hose 16. The reference gas chamber 18 thus has an internal pressure equal to that of the hyperbaric chamber 14, but the two chambers 14 and 18 are sealed from each other. The high purity oxygen thus cannot enter the reference gas chamber 18.

A hose 38 connects the hose 12 with a three way valve 32; a hose 37 connects the manifold with the valve 32; and a hose 26 connects the positive side of the transducer 4 with the valve 32. The hose 20 connects the hose 16 with the negative side of the transducer 4. A hose 28 connects the hose 12 with another three way valve 30 and with a hose 40, which connects with a two way valve 31. A hose 35 connects the valve 31 with the manifold 8 and a hose 34 connects the valve 30 with the manifold 8. The pressure side of the pump connects with the valve 30 via hose 42 and the supply side of the pump 6 connects with the manifold 8 via hose 41.

DESCRIPTION OF SPECIFIC EMBODIMENTS

The device operates as follows. First, the three way valve 32 is actuated to connect hoses 37 and 26. The positive side and the negative side of the of the transducer 4 are thus connected with each other through the hose 26, the valve 32, the hose 37, the manifold 8, the hose 22, the hose 16 and the hose 20. The electronic components 10 then check the output value of the transducer 4. The output value of the transducer 4 is used as a zero reference pressure for each subsequent measurement. Then the valve 32 is actuated to connect hose 26 with hose 38. When the cuff 36 is to be inflated, the gas flow is from the reference gas chamber 18 through hose 16, hose 22, manifold 8, and hose 41 to the supply side of the pump 6. The gas flow from the pressure side of the pump 6 to the cuff 36 is through hose 42, three way valve 30, which connects hose 42 with hose 28, hose 12 and hose 39. The pump 6 is operable to inflate the cuff 36. The gas used to inflate the cuff 36 is thus pumped from the reference gas chamber 18 into cuff 36. The reference pressure for determining the $\Delta P$ in the cuff 36 is the pressure in the hyperbaric chamber 14, which is sensed by the negative/reference side of the pressure transducer 4 through hose 16 and hose 20. The pressure in the cuff 36 is sensed by the positive side of the transducer 4 through hose 26, valve 32, hose 38, hose 12 and hose 39. When a predetermined $\Delta P$ is reached, the pump 6 is deactivated, and the valves 31 and 30 are actuated to begin to deflate the cuff 36. The deflation may be continuous or may be done stepwise, as taught by the prior art. The cuff pressure is sensed by the transducer 4, and arterial oscillations in the cuff pressure are also sensed by the transducer 4 in a conventional manner. Depending on the deflation protocol, either valve 30 or valve 31 is opened. In the first case, (with the valve 30 opened) gas flows from the cuff 36 through the hose 39, hose 12, hose 28, hose 34; and in the second case (with the valve 31 opened) through hose 35; and in both cases then through the manifold 8, hose 22, hose 16, back into the reference gas chamber 18. One of the valves 30, or 31, is larger than the other, so that the device can be used with both adult and pediatric cuffs.

The device of this invention can be used with any automatic blood pressure monitor, as for example, with monitors using auscultatory, oscillometric, ultrasonic, photoplethysmographic or the like techniques. The device could be used with a lower than ambient pressure chamber, should such a chamber prove useful in treating human maladies. The device allows constant blood pressure monitoring of patients in hyperbaric chambers thereby extending the utility of such chambers for the treatment of humans. The device operates without exposing any of the electrical components thereof to the high purity oxygen in the hyperbaric chamber.

Since many changes and variations of the disclosed embodiment of the invention may be made without departing from the inventive concept, it is not intended to limit the invention otherwise than as required by the appended claims.

What is claimed is:

1. An assembly for measuring the blood pressure of a subject disposed in a hyperbaric chamber containing high purity oxygen whose internal pressure is higher than atmospheric pressure, said assembly comprising:
   a) a cuff in the chamber for securement to an appendage of the subject;
   b) means located externally of the chamber for inflating said cuff;
   c) means located externally of the chamber for sensing and storing cuff pressure values, said means for sensing and storing including a differential pressure transducer;
   d) means for connecting a pressure sensing side of said differential pressure transducer with the interior of said cuff; and
   e) means for connecting a reference side of said differential pressure transducer to a pressure source having a gas pressure equal to that of the interior of the chamber, but which pressure source is free of high purity oxygen.

2. The assembly of claim 1 further including means for connecting said means for inflating to said pressure source whereby said cuff is inflated with gas from said pressure source.

3. The assembly of claim 2 further including means for exhausting inflation gas from said cuff, said means for exhausting being connected to said pressure source whereby gas from said cuff is exhausted to said pressure source.

4. The assembly of claim 1 wherein said pressure source is a flexible chamber disposed in said hyperbaric chamber.

* * * * *